United States Patent [19]

Iinuma

[11] 4,234,940
[45] Nov. 18, 1980

[54] ULTRASOUND TRANSMITTING OR RECEIVING APPARATUS

[75] Inventor: Kazuhiro Iinuma, Yokohama, Japan

[73] Assignee: Tokyo Shibaura Electric Co., Ltd., Japan

[21] Appl. No.: 887,337

[22] Filed: Mar. 16, 1978

[30] Foreign Application Priority Data

Mar. 16, 1977 [JP] Japan ................................. 52-28016

[51] Int. Cl.² .............................................. G01S 9/66
[52] U.S. Cl. ..................................... 367/105; 73/626; 343/100 SA
[58] Field of Search ................. 340/1 R; 343/100 SA; 73/620, 625, 626; 367/105

[56] References Cited

U.S. PATENT DOCUMENTS

| | | | |
|---|---|---|---|
| 4,080,838 | 3/1978 | Kuroda et al. | 340/1 R X |
| 4,099,419 | 7/1978 | Kuroda et al. | 340/1 R X |
| 4,116,229 | 9/1978 | Pering | 340/1 R X |
| 4,127,034 | 11/1978 | Lederman et al. | 73/626 |

OTHER PUBLICATIONS

O. T. von Ramm et al., *Cardiac Imaging Using a Phased Array Ultrasound System;* Circulation; vol. 53, No. 2, Feb. 1976.

*Primary Examiner*—T. H. Tubbesing
*Attorney, Agent, or Firm*—Finnegan, Henderson, Farabow, Garrett & Dunner

[57] ABSTRACT

In an ultrasound transmitting or receiving apparatus, a plurality of ultrasound transducer elements comprising an ultrasound probe are arranged along a line to transmit and receive ultrasonic waves. For the purpose of sequentially transmitting and receiving an ultrasound beam through the transducer elements, variable-delay circuits are provided for applying delay times to the transmitting signals and/or the received signals. The variable-delay circuits include memory control devices, the addresses of which correspond to the respective azimuthal directions of transmitting and receiving the ultrasound beam. The outputs of the memory devices are connected to control terminals of transfer switches, which in turn are connected to tapped delay lines. The memory devices produce control codes such that the tapped delay lines produce predetermined delay times which control the azimuthal directions of transmitting or receiving the ultrasound beam.

17 Claims, 10 Drawing Figures

ULTRASOUND TRANSMITTING OR RECEIVING APPARATUS

FIELD OF THE INVENTION

This invention relates to ultrasound transmitting or receiving apparatus of the electronic scanning type in which an acoustic wave is electronically scanned, and more particularly to an apparatus employing a sector scanning and compound scanning such that the azimuthal direction of transmission or reception of an acoustic wave is changed by phase control during the electronic scanning of an acoustic wave.

DESCRIPTION OF THE PRIOR ART

There have been used apparatus in which ultrasound pulses are transmitted into tissue areas under examination wherein the boundaries of different kinds of tissues which have respectively different acoustic impedance reflect the pulses and the echo signals derived from the reflections are utilized to image various planes of the tissues and to diagnose diseased regions of the tissues.

The method used in the apparatus mentioned above has been referred to as the pulse reflection method.

In the pulse reflection method, ultrasound pulses having a frequency of 2 MHz–10 MHz are transmitted into tissue areas from transducer elements and the acoustic waves reflected by a tissue boundary layers are detected for diagnostic purposes. This method is categorized according to the display system used. More particularly, when an A scope presentation is used the reflected waves are observed as an amplitude variation on a cathode ray tube, whereas when a B scope presentation is used the reflected waves are observed as a two-dimensional tomographic image represented by variations in the brightness of a cathode ray tube obtained by steering the ultrasound beam through a plane of the tissue structure under investigation by scanning a transducer. Furthermore, the pulse reflection method is also categorized according to the scanning system employed. With a linear scanning system, the ultrasound beam is steered in a parallel format and with a sector scanning system, the beam is steered in a circular sector format. With a compound scanning system, the linear scanning system and the sector scanning system are combined.

Ultrasound transmitting or receiving systems utilizing the pulse reflection method presently used to diagnose the presence or absence of bleeding in a brain caused by a head injury, various types of tumors, cholelithiasis and obstetrics. The sector scanning system is suitable for generating tomographic images of the heart. Therefore, there is a great need for ultrasound transmitting or receiving apparatus adapted for practical, reliable use.

In an electronic scanning type ultrasound transmitting or receiving apparatus, pulses may be applied to an array of transducer elements wherein the delay times are expressed by $(n-1)(d/c) \sin \theta$, $(n-2)(d/c) \sin \theta$, . . . 0, where $\theta$ represents the azimuthal angle in radians of the ultrasound beam, d represents the center to center distance between adjacent transducer elements, c represents the sound velocity (1,500 m/sec) in the medium, and n is the number of transducer elements. In this case the wavefronts of the ultrasound pulses generated by the respective transducer elements align on a straight line $A-A_1$ shown in FIG. 1, thereby transmitting an ultrasound beam in the direction of $\theta$.

During reception, echoes returning from targets in the direction of the transmitted pulses arrive at the transducer elements at different times. This necessitates delaying the received signals so that the effective orientation of the transducer element array during reception corresponds to the orientation during transmission.

Accordingly when the echo signals received by respective transducer elements are summed by a summing amplifier in phase after being adjusted by delay times identical to the delay times applied to the transmitted pulses, the acoustic waves received in the direction of $\theta$ can be detected as the strong signal, or as the summed echo signal from a desired azimuthal orientation. This signal is amplified by an amplifier, processed by a signal processing circuit and displayed by a display device.

Using sector scanning, the relative delay time applied to each transducer element is sequentially varied so as to scan by changing the azimuthal direction $\theta$ of transmission or reception of the ultrasound beam.

Accordingly, with sector scanning, it is important to apply the correct amount of delay time to each transducer element.

In order to change the azimuthal direction of the ultrasound beam the delay circuit should alter the time delay in each transducer element. Moreover, since the echo signal passes through the variable delay circuit as an electrical analog signal, the variable delay circuit should be an analog delay circuit. Among delay lines that can satisfy these requirements may be mentioned an LC delay line.

It, therefore, has been tried to use a tapped LC delay line, but the error of the delay time of such delay line is large so that it can not be used practically. When the tapped LC delay line is manufactured to have accurate delay time by decreasing the error, the delay line becomes extremely bulky and very expensive.

Where the delay time is accurately set, the frequency characteristic becomes irregular, while when the error of the delay time is large when the frequency characteristic is made to be flat.

For example, assuming that the spacing between adjacent transducer elements is d=0.5 mm, the number of the transducer elements is n=32, and the azimuthal angle of the ultrasound beam is $\theta=0.5°-40°$, the delay time between transducer elements would be from 3 nano sec. to 6.6 microseconds. Thus, the ratio between the minimum delay time and the maximum delay time would be 2,000. Since the delay time varies in such a wide range, it may be represented in terms of a quantum delay time. Various methods of quantizing the delay time have been used in the radar field, especially in phased array antenna systems or the like. Strictly speaking, in the case of an antenna, the quantum object is not the delay time but the phase, as is commonly recognized in the art. Quantization in the phased array antenna art is described in detail in Skolnik, "Radar Handbook" published by McGraw-Hill Inc., 1970, pages 11–35 and 11–43.

Where the quantum delay time is expressed by $\tau$, all the necessary delay times can be quantized and expressed as approximate values which are integral multiples of $\tau$. The quantum delay time $\tau$ should be less than $1/10-1/20$ of the period $T_0$ (reciprocal of frequency $f_0$ of the ultrasound pulse). Accordingly, the absolute error of the delay time of the delay circuit must be less than $T_0/10-T_0/20$.

For example, where the frequency of the ultrasound pulse is $f_0 = 2.5$ MHz, and the absolute error of the delay time is equal to $T_0/16$, then the period $T_0 = 400$ nano sec. so that less than nano seconds ($T_0/16$) is necessary for the error of the delay time. Expressing the allowable error time in terms of relative error, $$\frac{25 \text{ nano sec.}}{6,600 \text{ nano sec.}} \times 100 = 0.38\%.$$

The relative error accuracy of a commercial LC delay line capable of producing a delay time on the order of several microseconds is ordinaly about $\pm 2\% \sim \pm 5\%$. With this accuracy, therefore, the error of the delay time is large so that it is difficult to obtain high quality tomographic images due to the errors introduced in the azimuthal direction of transmission and reception of the ultrasound beam, and also due to the large side lobe which represents the transmission or reception of the ultrasound beam in directions other than the direction of the main beam.

In ultrasound receiving systems provided with delay circuits comprising tapped LC delay lines, it has been proposed to connect in cascade a number of delay circuits for obtaining a composite reflected signal as shown in FIG. 2.

In this regard, reference is made to the paper "Receiving System of Electronic Sector Scanning System," presented before the Japan Ultrasound Medical Society, May, 1976.

According to this system, reflected acoustic waves received by transducer elements $T_1, T_2 \ldots T_n$ are summed by passing them through delay circuits $D_1, D_2 \ldots D_n$ and summing amplifiers $SA_1, SA_2 \ldots SA_n$ and then displaying the composite return on a display device 14 through an amplifier (12) and a signal processing circuit 13 after modulating the brightness, as shown in FIG. 2. In this apparatus, the delay times of the delay circuits $D_1, D_2 \ldots D_{n-1}$ are adjusted to be equal so as to obtain an ultrasound beam in the direction of $\theta$ (ultrasound azimuthal direction).

As the azimuthal angle $\theta$ varies, the delay times of the delay circuits $D_1, D_2 \ldots D_{n-1}$ vary to effect scanning.

With this apparatus, however, it is difficult to accurately match the absolute values of the delay times. Accordingly, the azimuthal direction of reception might be different from the correct direction of the target.

For this reason, in such apparatus when different delay circuits are used for the transmission and reception of the acoustic wave, the azimuthal directions of transmission and reception often differ, thus substantially widening the beam width. Although not shown in FIG. 2 it is necessary to connect buffer amplifiers between adjacent delay lines. Since such amplifiers cause additional time delays, it is necessary to insert further correction delay circuits between transducer elements $T_1, T_2 \ldots T_n$ and the summing amplifiers $SA_1, SA_2 \ldots SA_n$ for the purpose of compensating for such time delays thus requiring a large number of different circuits. Moreover, as a plurality of delay circuits such as 16 or 32 circuits are connected in cascade, the frequency characteristics of the delay circuits $D_1, D_2 \ldots D_{n-1}$ are greatly degraded whereby it becomes impossible to obtain a flat frequency characteristic.

Accordingly, it is an object of this invention to provide an improved ultrasound transmitting or receiving apparatus which can eliminate various defects of the prior art apparatus, and has accurate delay times and can steer the azimuthal direction of the ultrasound beam correctly for a target.

According to this invention this object can be accomplished by providing an ultrasound transmitting or receiving apparatus in which a pair of variable delay circuits comprise tapped delay lines which generate an ordinal delay time, transfer switches which select taps by changing over the control terminals of the delay lines, and a memory connected to the control input terminals of the transfer switches. In the memory each address corresponds to a different azimuthal angle of transmission or reception of the ultrasound beam and data for establishing connections between the transfer switches and the control terminals of the delay lines is stored therein and read out in response to output signals generated by a scan control circuit. The data is applied to the transfer switches so that the delay circuits apply the required delay times to the transducer elements to obtain the predetermined azimuthal directions of transmission or reception of the beam.

This invention can be more fully understood from the following detailed description when taken in conjunction with the accompanying drawings, in which.

Ultrasound transmitting or receiving apparatus adapted for use in an ultrasound diagnostic system will now be described.

Figure 1:
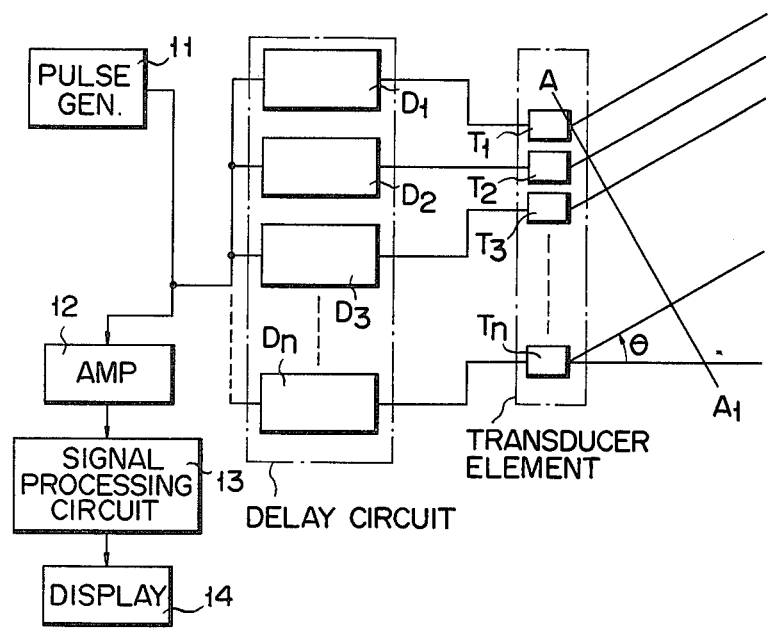
FIG. 1 is a block diagram for explaining electronic sector scanning.
Figure 2:
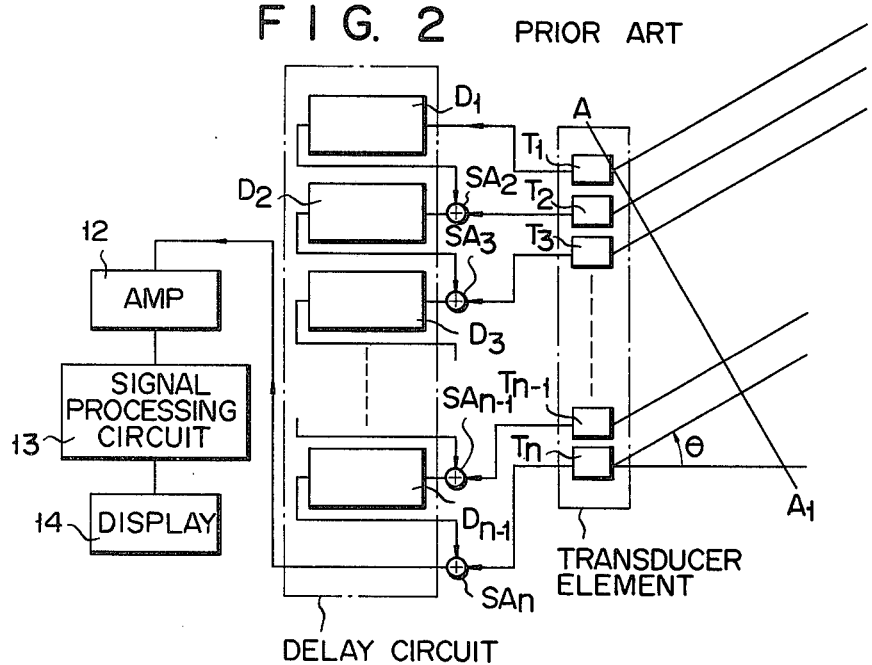
FIG. 2 is a block connection diagram showing a form of prior art sector scanning type ultrasound diagnosing apparatus.
Figure 3:
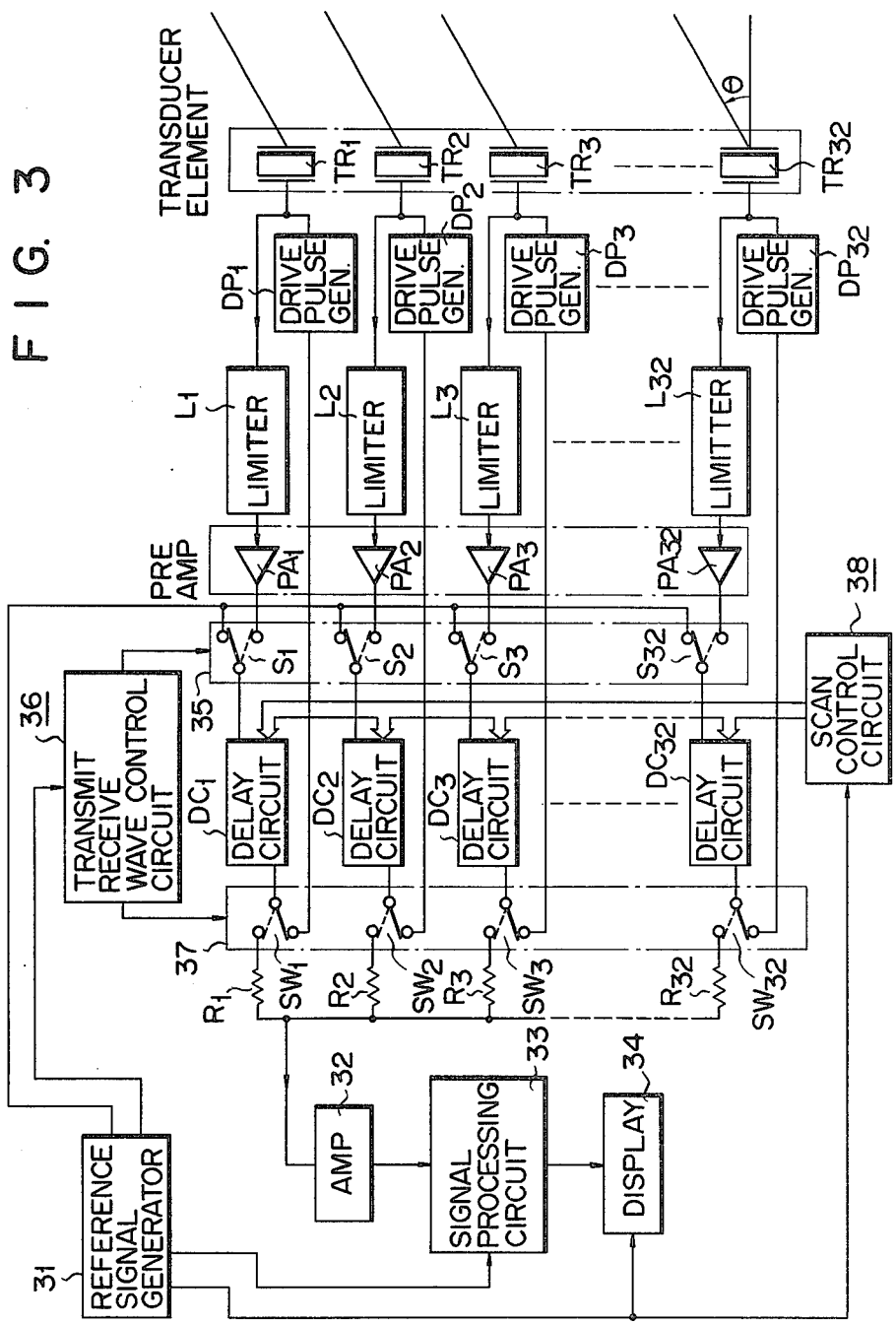
FIG. 3 is a block diagram showing one embodiment of an ultrasound diagnosing apparatus according to the invention.

Referring to FIG. 3, a plurality of transducer elements such as the thirty-two elements $TR_1$ through $TR_{32}$ are arranged in a line to transmit ultrasound pulses and to receive reflected ultrasonic waves. Respective elements are connected to the output terminals of driving pulse generators $DP_1$ through $DP_{32}$ and input terminals of limiters $L_1$ through $L_{32}$ through cables. The output terminals of limiters $L_1$ through $L_{32}$ are connected to the input terminals of corresponding preamplifiers $PA_1$ through $PA_{32}$. The output terminals of these preamplifiers $PA_1$ through $PA_{32}$, the output terminal of a reference signal generator 31 and the input terminal of delay circuits $DC_1$ through $DC_{32}$ are connected to respective analogue switches $S_1$ through $S_{32}$ of a switch group 35. In response to a control signal generated by a transmitting and receiving wave control circuit 36, respective variable delay circuits (hereinbelow referred to as delay circuit ) $DC_1$ through $DC_{32}$ receive a reference pulse generated by reference signal generator 31 or reflected ultrasound signals which have passed through preamplifiers $PA_1$ through $PA_{32}$. The analog switches $SW_1$ through $SW_{32}$ of the switch group 37 are controlled by the output signal of the transmitting and receiving wave control circuit 36 to be transfer switched in synchronism with switches $S_1$ through $S_{32}$ of switch group 35. Thus, when the input terminals of the delay circuits $DC_1$ through $DC_{32}$ are connected to the output terminal of reference signal generator 31 the output terminals of these delay circuits are transferred to the input terminals of driving pulse generators $DP_1$ through $DP_{32}$, whereas when the input terminals of the delay circuits $DC_1$ through $DC_{32}$ are connected to the output terminals of respective preamplifiers $PA_1$ through $PA_{32}$, the output terminals of the delay circuits $DC_1$ through $DC_{32}$ are connected to the input terminal of an amplifier 32 via resistors $R_1$ through $R_{32}$.

Figure 4:
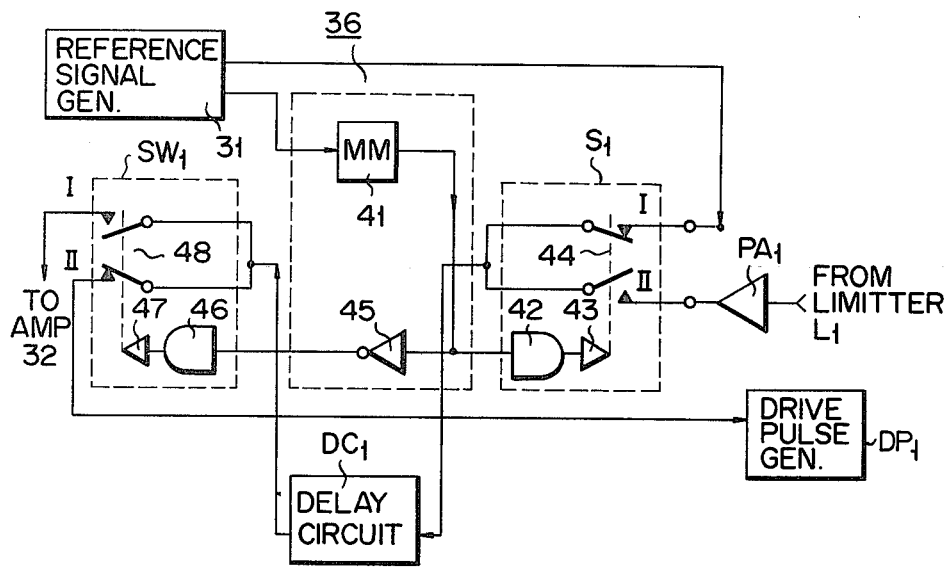
FIG. 4 is a block diagram showing a transmitting and receiving wave control circuit.

The relationship between the transmitting and receiving wave control circuit 36 and switch groups 35 and 37 will now be described. More particularly, as shown in FIG. 4, one output terminal of the reference signal generator 31 is connected to the input terminal of a monostable multivibrator 41 while the other output terminal is connected to analog switch $S_1$ of the switch group 35. The output terminal of the monostable multivibrator 41 is connected a control terminal of the analog switch $S_1$. The output terminal of the monostable multivibrator 41 is also connected to a control terminal of analog switch $SW_1$ of switch group 37 via an inverter 45. Furthermore, the common terminals of the analogue switches $S_1$ and $SW_1$ are connected to delay circuit $DC_1$. The control inputs of the switches include appropriate gate elements 42, 46, drive amplifiers 43, 47, and contact controls depicted by the dashed lines 44, 48. The contacts may be either mechanical or solid state. The switches $S_1$ and $SW_1$ may be implemented by, for example, a type SPOT analog switch DG 186 sold by Siliconix Inc.

Since the transmitting and receiving wave control circuit 36, the analog switches $S_1$ through $S_{32}$ and switches $SW_1$ through $SW_{32}$ of the switch groups 35 and 37 are constructed as above described, the operation of the transmitting and receiving wave control circuit 36 will now be described with reference to FIGS. 5a through 5f.

Figure 5:
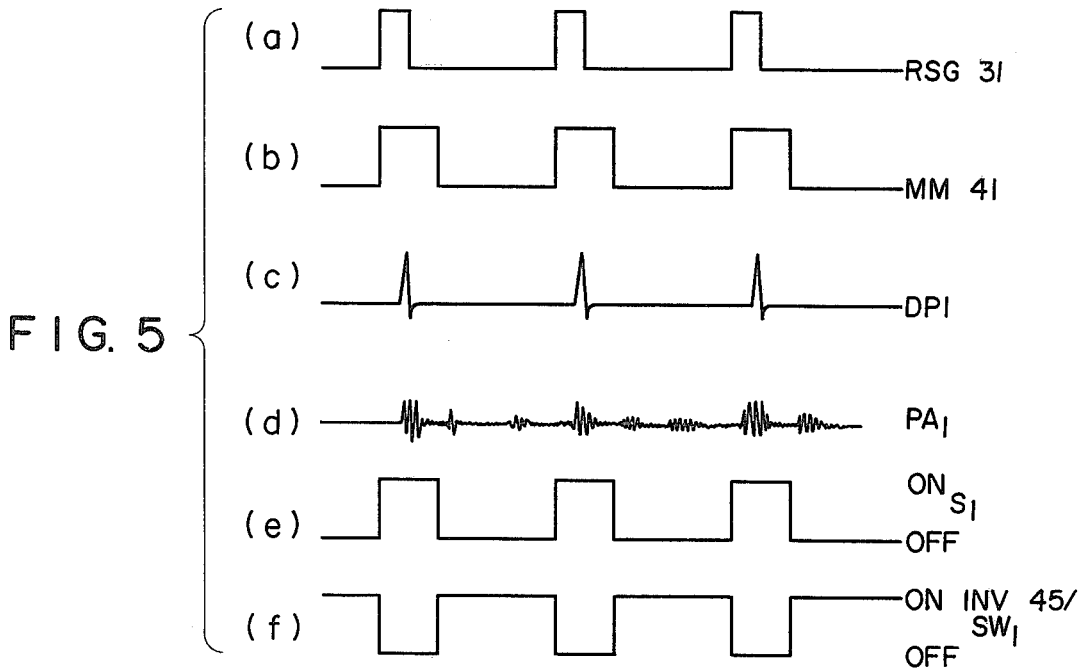
FIGS. 5a through 5f are waveform diagrams representing various signals in of the transmitting and receiving wave control circuit.

When the output signal generated by the reference signal generator 31 becomes high level as shown in FIG. 5a, the output of the multivibrator 41 becomes high level as shown by FIG. 5b, and upper contact I of the analog switch $S_1$ is switched to the ON state as shown in FIG. 5e so that the analog switch $S_1$ conducts through the upper contact I. However, the output of the inverter 45 shifts to the low level as shown in FIG. 5f thus throwing the analogue switch $SW_1$ to lower contact II. Consequently, the drive pulse generator $DP_1$ produces a pulse as shown in FIG. 5c delayed by the delay interval of $DC_1$. When a received wave signal as shown in FIG. 5d is applied to the preamplifier $PA_1$ the output of the monostable multivibrator 41 has switched to the low level whereas the output of the inverter 45 is high. As a consequence, the analog switch $S_1$ is thrown to the lower contact II and the analogue switch $SW_1$ to the upper contact I.

The received ultrasound signals are summed together by the resistor circuits ($R_1$, $R_2$ . . . $R_n$), amplified by amplifier 32 and then detected by the signal processing circuit 33. The construction and operation of the signal processing circuit 33 is described in detail in P.N.T. Wells, "Physical Principle of Ultrasonic Diagnosis" Academic Press (1969), page 108, FIGS. 4, 12.

The signal processed by the signal processing circuit 33 is displayed by display device 34 and provides an image of the tissue area under examination.

Figure 6:
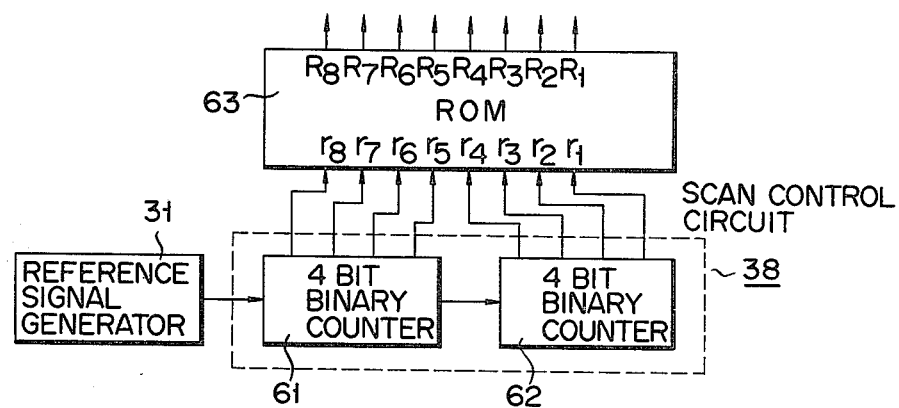
FIG. 6 is a block diagram showing a scanning control circuit.

The operating timing of the transmitting and receiving wave control circuit 36, the scanning control circuit 38, the signal processing circuit 33 and the display device 34 is controlled by the signal generated by the reference signal generating circuit 31. The delay times of the input signals provided by the delay circuits $DC_1$ through $DC_{32}$ are controlled by the scanning control circuit 38 which in one form comprises a pair of binary counters 61 and 62 as shown by FIG. 6.

Where transmitting acoustic waves and receiving the echo signals from many different azimuthal directions, e.g., 256, the simplest construction comprises two binary counters 61 and 62, as shown in FIG. 6. The counters each contain 4 bits and are connected in series and their outputs are suapplied to 8 bit input terminals $r_1$ through $r_8$ of a read only memory device 63. When a rate pulse generated by the reference signal generator 31 is applied to the binary counters 61 and 62, these counters count up one by one to designate by repetition of codes 00000000, 00000001, 00000010 . . . 11111111 the addresses of the read only memory device 63, whereby 256 scanning lines are designated. Type SN74193 binary counter sold by Texas Instrument Co. is suitable as the 4 bit binary counters 61 and 62.

The manner of setting the delay times of delay circuits $DC_1$ through $DC_{32}$ by the output signal of the scanning control circuit 38 will now be described with reference to FIG. 7 by taking one delay circuit $DC_1$ for one channel as an example.

Figure 7:
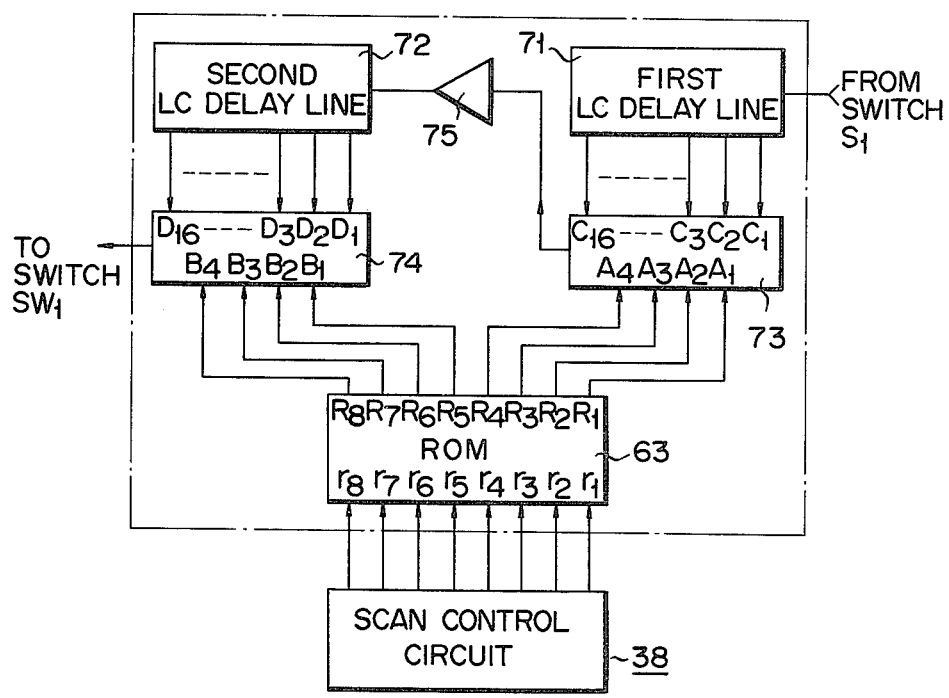
FIG. 7 is a connection diagram showing a portion of the embodiment illustrated in FIG. 3.

As shown in FIG. 7, the delay circuit $DC_1$ comprises first and second tapped LC delay lines 71 and 72 each provided with 16 output taps, first and second identical transfer switches 73 and 74, each provided with 16 input terminals respectively connected to the 16 output terminals of the delay line, and one output terminal. The outputs of read only memory device 63 are connected to 4 control input terminals $A_1$ through $A_4$ and $B_1$ through $B_4$ of the respective transfer switches 73 and 74, and a buffer amplifier 75 is connected between the output terminal of the first transfer switch 73 and the input of the second tapped LC delay line 72. The circuit elements bounded by the dot-dash lines are formed, in one embodiment, on the same printed circuit board.

The first tapped LC delay line 71 has a 25 nano second intertap delay time so that its delay time can be varied in the range of from 0 to 375 nano seconds by the transfer operation of the first transfer switch 73, and its error is ±10 nano seconds for the maximum delay time of 375 nano seconds. The relative error of the delay time is thus ±2.7% and a delay line having such accuracy can readily be manufactured.

The second tapped LC delay line 72 has an intertap delay time of 380 nano seconds which is substantially equal to the maximum delay time of the first tapped LC delay line 71. The intertap delay time error of the delay line 72 is about ±10 nano seconds which is variable in the range of from 0 to 5.7 microseconds. The delay line 72 has an error of ±150 nano seconds for the maximum delay time of 5.7 microseconds, which represents a relative error of ±2.6%. Such delay line can also be readily manufactured.

Type DG506 transfer switch manufactured by Siliconix Inc. may be used to implement the first and second transfer switches 73 and 74. The transfer of the respective switches $C_1$ through $C_{16}$ and $D_1$ through $D_{16}$ (corresponding to the output taps of the delay lines) of the transfer switches 73 and 74 is controlled by a binary signal supplied to the control input terminals $A_1$ through $A_4$ and $B_1$ through $B_4$ from the read only memory device 63.

The contents of the memory device may be derived in accordance with the equation:

$$(n-1)(d/c) \sin \theta, (n-2)(d/c) \sin \theta, \ldots 0,$$

where $\theta$ represents the azimuthal angle of the beam in radians, d represents the center to center distance between adjacent transducer elements, c represents the velocity of sound (e.g., 1500 m/sec.) in the medium, and n is the number of transducer elements.

Thus, optimum delay times are predetermined by an equation corresponding to respective azimuthal angles of the transmission and reception of the ultrasound, and respective addresses of the read only memory device are made to correspond to specific angles of the directions of acoustic wave transmission and reception. Control information is written into the read only memory device which controls the first and second transfer switches 73 and 74 such that the first and second tapped LC delay lines 71 and 72 produce delay times which are closest to the optimum delay times.

Although in the foregoing description, only the delay circuit $DC_1$ was described, the same construction is used for the other delay circuits $DC_2$ through $DC_{32}$.

Since the intertap delay times of the tapped delay lines 71 and 72 have errors depending on the delay lines used as above described, the contents of the read only memory device 63 of the same channel may differ depending upon the LC delay line employed.

For example, in the illustrated apparatus, where an ultrasound beam is transmitted and received in 256 different directions $\theta$, the scanning control circuit 38 applies to the read only memory device 63 of respective delay circuits $DC_1$ through $DC_{32}$ an 8 bit binary signal corresponding to respective angles of $\theta_{128}$ through $-\theta_{128}$ (total 256 angles). Each read only memory device applies the control input signals which have been stored in respective addresses to the control input terminals of the first and second transfer switches 73 and 74 whereby the delay circuits $DC_1$ through $DC_{32}$ are controlled to generate delay times which are closest to the correct delay time necessary to transmit and receive the ultrasonic wave in the designated directions.

For example, as shown in FIG. 8a, where an ultrasound beam is transmitted from an array of transducer elements $TR_1$ through $TR_{32}$ in the direction of $\theta_{128}$ and the wave receiving directivity is in this direction (hereinafter termed deflection in the direction of $\theta_{128}$), the output signal of the scanning control circuit 38 would be 00000000. At this time, in this address of the read only memory devices 63 for each delay circuit $DC_1$-$DC_{32}$ is stored a control signal showing a specific setting of the first and second transfer switches 73 and 74 which gives a delay time which is closest to that required at that time.

As shown in FIG. 8b, where deflection is made in the direction of $\theta_{128}$, the delay time applied to the channel associated with transducer element $TR_1$ is the maximum. At this time, the read only memory device 63 of the delay circuit $DC_1$ produces a control signal that connects selectively the switches $C_{16}$ and $D_{16}$ of the first and second transfer switches 73 and 74.

However, as the first and second tapped LC delay lines 71 and 72 have errors respectively as above described, it is not always certain that delay lines 71 and 72 of the delay circuit $DC_1$ will give delay times closest to the optimum delay time when switch positions $C_{16}$ and $D_{16}$ are transferred.

Since as above described the first and second tapped delay lines 71 and 72 have delay time errors of less than ±150 nano seconds it is necessary to measure times when the switch terminals of the transfer switches 73 and 74 are connected to the taps of the delay lines 71 and 72 for storing combinations of the taps of the analog switches that produce delay times closest to required delay times for respective angular directions in the addresses of the read only memory device corresponding to respective angles.

Where electronic focusing (referred to in U.S. Pat. No. 3,914,683, for example) is added to sector scanning, the adjustment of required delay delay times is shown by the dot-dash line in the azimuthal direction of $\theta_{128}$ in FIG. 8b. Though the electronic focusing delay times are generally added to electronic scanning, only the delay time for controlling directivity will be described hereinbelow.

Where a delay circuit including a combination of the read only memory device 63 storing the above described code, the tapped LC delay line and the transfer switch is used, the delay circuit will produce necessary delay times at sufficiently high accuracies with reference to the address of the read only memory device 63 irrespective of poor accuracy of the LC delay line itself.

The transfer switch terminal numbers to be selected are stored in the read only memory device 63 in the following manner.

Figure 9:
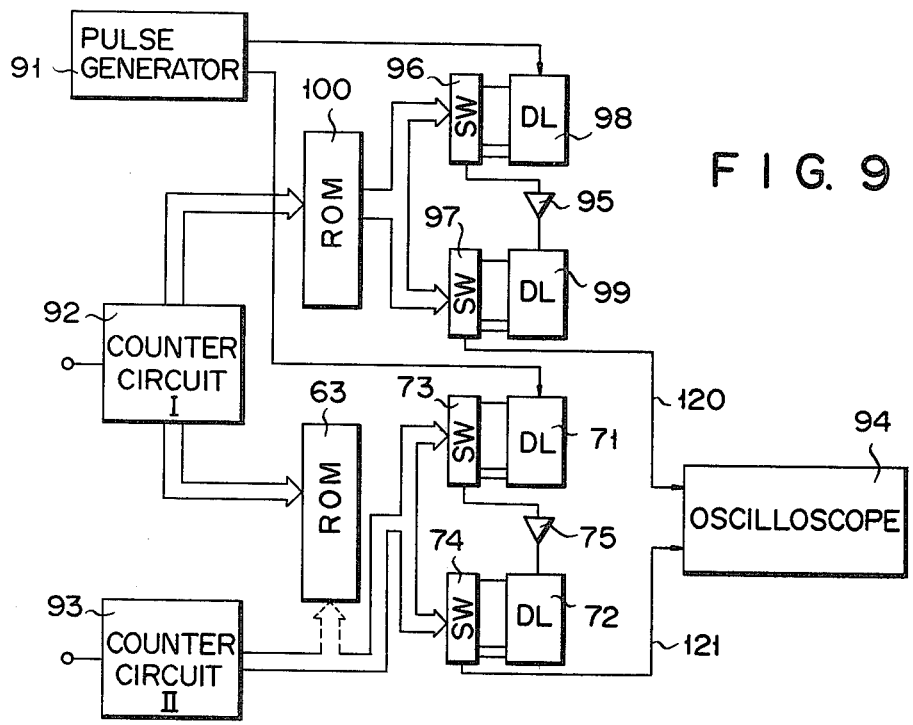
FIG. 9 is a block diagram showing the manner of storing the combinations of the taps of tapped delay lines in a read only memory device.

As shown in FIG. 9, delay circuits $DC_1$ through $DC_{32}$ are represented by circuit elements similar thereto. In addition, a pulse generator 91, counter circuit I (92), counter circuit II (93), and an oscilloscope 94 are provided. The delay circuit including tapped delay lines 98 and 99 is a special precision-built calibration unit used for setting the required delay times of the operating circuits $DC_1$-$DC_{32}$. The addresses of read only memory device 100 are constituted by 8 bits and its outputs are constituted by 10 bits.

Transfer of the 32 switch terminals of the transfer switches 96 and 97 is controlled by 5 bit input signals. A buffer amplifier 95 is connected between the first transfer switch 96 and the second tapped delay line 99.

Each of the first and second tapped delay lines 98 and 99 is provided with 32 taps. The intertap delay time of the first tapped delay line 98 is 6.25 nano seconds, whereas that of the second tapped delay line 99 is 200 nano seconds. Furthermore, these delay lines are substantially free from any delay time error. Surface wave delay lines can be used for this purpose.

The necessary delay times at sufficiently high accuracies produced by the first and second tapped delay lines 98, 99 will be displayed on the scope 94 and the taps of the first and second tapped LC delay lines 71, 72 are selected in order to produce the same amounts of delay time.

The pulse generator 91 generates an impulse train having a repetition frequency of 1 KHz, for example. The counter circuit I 92 comprises 8 bits and its output is incremented one by one by a manually operated switch to designate the addresses of read only memory devices 100 and 63. The former stores the address of a switch terminal that gives a delay time closest to the delay time required by each address.

At first the counter circuit I (92) sets the address of the read only memory device 100 to 00000000. At this time, the terminals of the transfer switches 96 and 97 controlled by each 1-bit in the output of the read only memory corresponding to this address 00000000 are switched to the ON state.

The impulse generated by the pulse generator 91 is delayed an accurately measured, correct delay interval by delay lines 98 and 99 and displayed on oscilloscope 94.

Then, the number of counts of the counter II (93) is manually adjusted so that the impulse displayed on the oscilloscope through delay lines 71 and 72 is superimposed upon the displayed impulse from delay lines 98 and 99, and the count of the counter circuit II (93) when these impulses coincide with each other is stored in an address of the read only memory device 63 which may, for example, be a programmable read only memory (PROM) circuit. Next, the switch of the counter circuit I (92) is operated to designate the next address 00000001 of the read only memory devices 100 and 63. In the same manner, a suitable delay value is programmed into the read only memory device 63. The memory device which has been provided with suitable values for the delay lines 71 and 72 utilized at that time in its 256 addresses is incorporated into the apparatus shown in FIG. 3 together with the transfer switches 73 and 74, and the delay lines 71 and 72 utilized at that time. The calibration operation described above is performed for each of the delay circuits and associated memory devices used in the system of FIG. 3.

Besides the method described above, there are various additional methods for entering suitable values into read only memory 63. For example, data obtained by measuring each intertap delay time (32 measurements for each channel) of the tapped LC delay lines 71 and 72 can be used by a computer to accurately calculate the required delay intervals and the output of the computer may then be directly written into the read only memory 63.

The embodiment shown in FIGS. 3 and 7 operates as follows.

The output signal of the transmitting and receiving wave control circuit 36 controls the switches of the switch group 35 such that they are transferred to the upper contacts and the switches of the switch group 37 such that they are transferred to the lower contacts.

Figure 8:
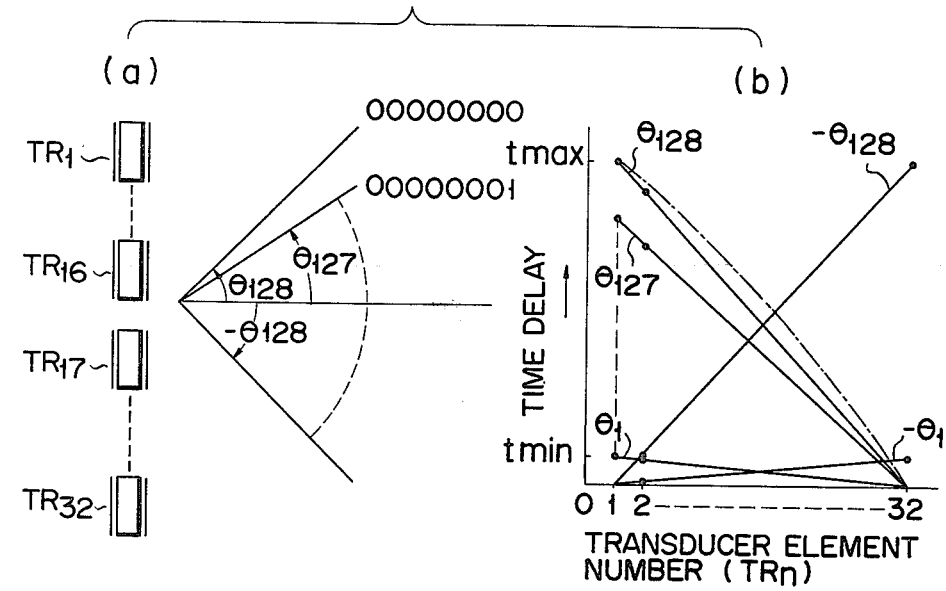
FIG. 8a is a schematic diagram demonstrating the relationship between the deflection angle $\theta$ of the ultrasound beam and the addresses of a memory device corresponding to the deflection angle $\theta$.
FIG. 8b is a graph showing the relationship between the deflection angle $\theta$ and the delay time of respective transducer elements.

The scanning control circuit 38 produces an 8 bit signal corresponding to the ultrasound azimuthal angle $\theta_{128}$ and each read only memory device 63 of each of the delay circuits $DC_1$ through $DC_{32}$ designates the same address 00000000. The output signal from the read only memory devices 63 designate the switch combination most suitable for the delay time required to be applied to respective channels of transducer elements $TR_1$ through $TR_{32}$ via the first and second transfer switches 73 and 74. The designated terminals of the transfer switches 73 and 74 are switched to the ON state so that the pulse generated by the reference signal generator 31 is applied to the driving pulse generators $DP_1$ through $DP_{32}$ passing through the delay circuits $DC_1$ through $DC_{32}$, with suitable time delays imposed thereby, thus driving the transducer elements $TR_1$ through $TR_{32}$. Since the per channel delay time decreases in sequential order from delay circuit $DC_1$ to delay circuit $DC_{32}$, the transducer elements are driven in sequence from $TR_{32}$ to $TR_1$ with the result that the ultrasound beam is transmitted in the direction of $\theta_{128}$ (FIG. 8).

Thereafter, the output signal from the transmitting and receiving wave control circuit 36 is applied through the switches of the switch groups 35 and 37 respectively to the lower and upper contacts. The reflected ultrasound signals received by the transducer elements $TR_1$ through $TR_{32}$ are amplified by preamplifiers $PA_1$ through $PA_{32}$, delayed by delay circuits $DC_1$ through $DC_{32}$ in the same manner as in the case of transmission and then summed. The azimuthal steering of the received acoustic wave is in the direction of $\theta_{128}$.

Limiters $L_1$ through $L_{32}$ limit the high voltage transmitting pulses applied to the inputs of the preamplfiers $PA_1$ through $PA_{32}$ during the transmit cycle.

The summed signal is amplified by amplifier 32, detected by signal processing circuit 33 and then displayed on display device 34 as a signal corresponding to the direction $\theta_{128}$ after it has been subjected to brightness modulation in accordance with known principles.

Next, the output signal from the transmitting and receiving wave control circuit 36 transfers the switches of switch groups 35 and 37 to the upper and lower contacts respectively, while the scanning control circuit 38 produces an 8 bit signal 00000001 corresponding to $\theta_{127}$. Suitable terminals of the first and second transfer switches 73 and 74 of each delay circuit are selected by the output signal of the read only memories 63 to obtain the delay times required to control the direction of transmission $\theta_{127}$ of the ultrasound beam.

Thereafter, the reference pulse generated by the reference signal generator 31 is applied to respective driving pulse generators $DP_1$ through $DP_{32}$ via delay circuits $DC_1$ through $DC_{32}$ so that the transducer elements $TR_1$ through $TR_{32}$ transmit the ultrasound beam in the direction of $\theta_{127}$. In the same manner, scanning of the ultrasound is continued until angle $-\theta_{128}$ is reached.

In this embodiment, the delay circuit is constituted by a first tapped LC delay line having a shorter overall delay time and a second tapped LC delay line having an intertap delay time substantially equal to the overall delay time of the first tapped LC delay line and a longer overall delay time, and further having lower absolute accuracy. By the use of two kinds of tapped LC delay line, it is possible to greatly decrease the number of taps required compared to the case where the delay circuit employs a single tapped LC delay line.

For example, with a single delay line, 256 taps are necessary to provide an intertap delay time of 25 nano seconds and a maximum delay time of 6.4 microseconds whereas when two delay lines are used only 32 taps are necessary. Where 4 delay lines are used, the total number of taps is only 16. However, use of too many separate delay lines makes it difficult to establish proper connections therebetween. When two delay lines are used to obtain 256 delay times, provision of 16 taps for each gives a minimum total number of taps.

Although in the foregoing embodiment, the long-delay tapped LC delay line was connected "downstream" of the short-delay tapped LC delay line, their order of connection may be reversed.

In the embodiment described above since the same apparatus is used in common for the transmission and reception of the wave the beam directions generated for transmission and reception coincide with each other, thus assuring excellent characteristics. When the elements shown in FIG. 7 are formed on the same printed circuit board, such assembly produces a high quality delay line and furthermore facilitates its wiring, because a common address is supplied to the read only memory devices 63 for all delay circuits $DC_1$ through $DC_{32}$. As calibration of the delay circuits is performed on the printed circuit board with each electronic circuit elements assembled in the form in which they are to be used in the final system, the delay times can be very accurately controlled. Furthermore, the frequency characteristic of the delay circuits is easily extended up to 4 MHz.

Although in the foregoing embodiment the invention was applied to an ultrasonic diagnostic apparatus comprising transmit and receive circuits, it is possible to apply the invention only to the transmitting apparatus and also it is possible to use a digital apparatus for transmission and to apply the invention only to the receiving apparatus.

Furthermore, although in the foregoing embodiment, separate driving pulse generators are provided for each ultrasound transducer element, it is possible to use only one driving pulse generator and apply the output of the generator to all the variable delay circuits in parallel.

It should also be understood that the invention is not limited to a sector scanning type of system but is also applicable to a combination of linear scanning and sector scanning systems.

By applying electronic focusing to the ultrasound diagnosing apparatus described above, it has the great advantage of producing high quality tomographic images.

According to this invention even when tapped delay lines having ordinary delay time accuracy are employed which is not sufficient to attain the object of this invention, it is possible to obtain a sufficiently accurate delay time without deteriorating the frequency characteristic, and also it is possible to steer the ultrasonic waves sufficiently accurately to obtain the desired azimuthal beam directions in the transmission and reception operations.

Moreover where a tapped LC delay line is used as the delay line above described, it is easy to obtain a dynamic range above 100 db so that the circuit elements and peripheral apparatus can be greatly simplified. As the delay interval is determined solely by the address of the memory device and since the address is common to all channels, the number of connecting wires can be greatly reduced thus simplifying the control circuit. Since adjustments can be made on a channel-by-channel basis, it can be made and maintained very readily.

Furthermore according to this invention there is an irregularity in the delay time error so that quantization becomes random. This eliminates the regularity of the quantization error. This is advantageous in that the quantization side lobe can be decreased.

It should be understood that the invention is not limited to the embodiments described and that many variations and modifications may be made without departing the true spirit and scope of the invention.

Figure 10:
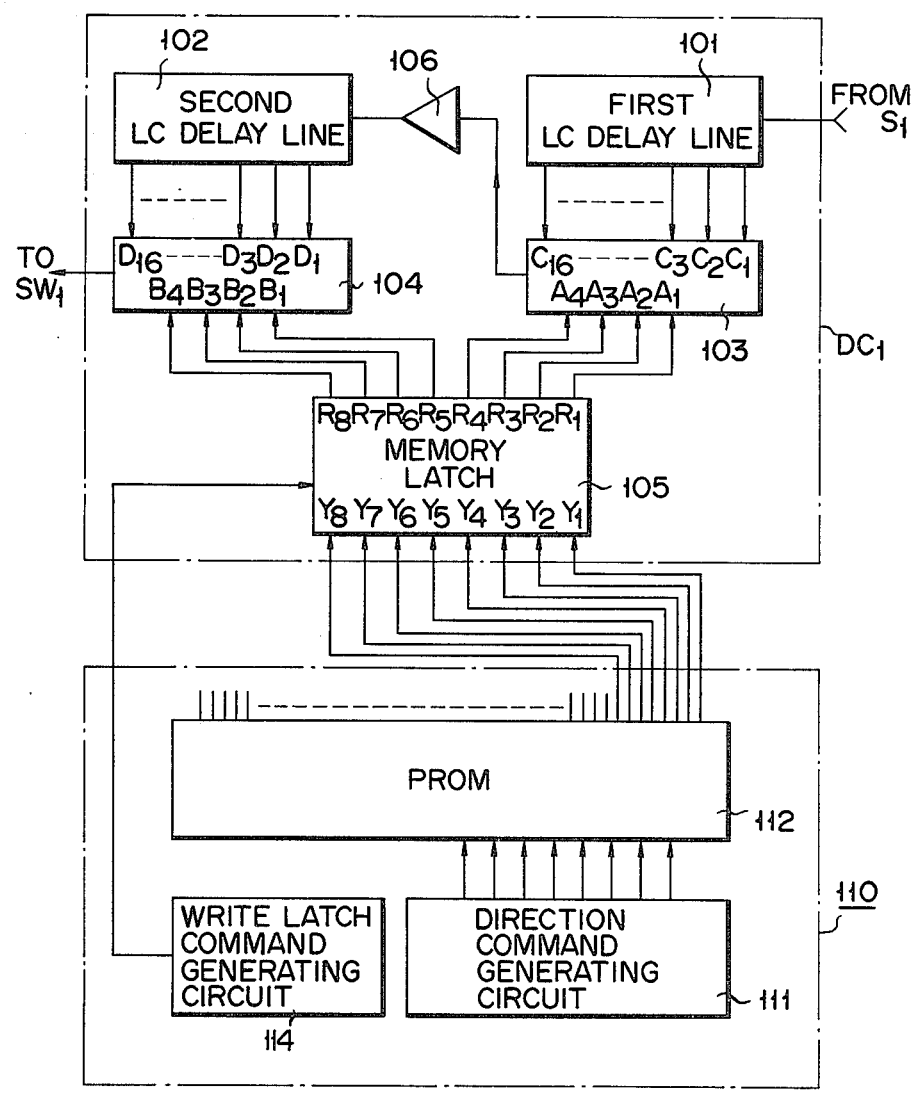
FIG. 10 is a block diagram showing a modified embodiment according to the invention.

For example, FIG. 10 shows another embodiment of this invention. In this embodiment each delay circuit such as $DC_1$ is constituted by first and second tapped LC delay lines 101 and 102 each having 16 output taps, first and second identical transfer switches 103 and 104, each having 16 inputs respectively connected to the 16 output taps of the delay lines, a memory latch 105 connected to the four control input terminals $A_1$ through $A_4$ and $B_1$ through $B_4$ respectively of each of the transfer switches, and a buffer amplifier 106 connected between the output terminal of the first transfer switch 103 and the input terminal of the second tapped LC delay line 102. These elements are formed on the same printed circuit board.

The scanning control circuit 110 comprises a direction designation circuit 111 that designates the direction of transmitting and receiving the ultrasonic wave, a programmable read only memory device (PROM) 112 (whose contents can be updated) storing the switch numbers that give delay times sufficiently close to the delay times to be given to respective delay circuits $DC_1$ through $DC_{32}$ by utilizing the direction designated by the direction command circuit, and a writing latch designation circuit 114 which writes the data in a latch circuit 105 on each printed circuit board for each rate pulse. The output of the PROM 112 is applied to the input terminal of the memory latch 105 of respective delay circuits $DC_1$ through $DC_{32}$. With the scanning control circuit 110 described above, the direction designation circuit 111 produces an 8 bit signal 00000000 corresponding to the azimuthal angle $\theta_{128}$ of the ultrasonic wave, and the PROM 112 applies a combination of switch numbers to be selected of respective delay circuits $DC_1$ through $DC_{32}$ to the memory latch of each respective delay circuit $DC_1$ through $DC_{32}$. In response to the rate pulse from the reference signal generator 31, the output signal of the writing latch designation circuit 114 is applied to the memory latch 105 to write the output signal of the PROM 112 into the memory latch circuit 105.

With the construction described above, all top positions to be selected for the tapped delay lines of all delay circuits is stored in the single read only memory device 112. Each delay circuit can be readily manufactured at a low cost since the tap position stored in the read only memory circuit can be preserved by a memory latch circuit. Furthermore by modifying the contents of the single read only memory device, changes in the scanning direction, provision of the delays for focusing and alteration of the delay intervals for other purposes is readily accomplished.

Programmable read only memory or erasable programmable read only memory are included in read only memory. In this invention, since the contents of read only memories are generally different depending on delay lines, the programmable read only memory or erasable programmable read only memory are extremely convenient for use.

In the invention, described above, various kinds of memory devices such as read only memory device, memory latch circuit etc. can be used for the memory device used in the different delay circuits.

Instead of forming the address of the read only memory device with 8 bits for designating 256 scanning directions of the ultrasonic beam, higher quality tomographic images can be obtained by an ultrasound diagnosing apparatus which comprises a transmitting or receiving apparatus in which 256 directions are encoded with 8 bits out of 10 bits that form the address of the read only memory and the remaining two bits are used to convey focusing information. The latter may be used, for example, to adjust the four-bit code applied to the transfer switch of the short-delay LC delay line, whereby the delay interval is altered incrementally for focusing purposes.

What is claimed is:

1. A beam steering system for an ultrasonic diagnostic apparatus comprising, in combination:
   a plurality of ultrasound transducers for generating an ultrasonic beam;
   pulse generating means for energizing said transducers to emit a sequence of pulses of ultrasonic energy;
   a plurality of variable delay circuits for coupling said pulse generating means to each of said transducers, each said variable delay circuit including a tapped analog delay line having an input connected to receive the output of said pulse generating means and a plurality of output taps, said circuit further including an analog switch connected to each said tap and to a common output coupled to one of said transducers and a memory storing switch control codes representing states of said analog tap switches, said memory including an output connected to control said switches; and
   a scan control circuit connected to said memories of said variable delay circuits and constructed and arranged to generate a succession of scan signals each of which represent a particular beam direction, each of said signals operating to access an address of said memories and to apply the switch control code stored at said address to the associated analog tap switches, whereby said transducers are pulsed at predetermined times for generating an ultrasonic beam in a direction controlled by said scan control circuit.

2. The apparatus according to claim 1 wherein said tapped analog delay line, said switches and said memory are arranged proximate to each other on a common circuit board.

3. The apparatus according to claim 1 wherein said tapped analog delay line comprises a first delay line having an intertap delay time approximately equal to a quantum delay time and a second delay line having an intertap delay time approximately equal to the overall delay time of said first delay line and an overall delay time longer than that of said first delay line and having the delay time required to give a maximum deflection angle of the ultrasonic beam directivity.

4. The apparatus according to claim 3 wherein said first and second analog delay lines are each provided with 16 taps.

5. The apparatus according to claim 1 wherein said tapped analog delay line comprises an LC delay line.

6. The apparatus according to claim 1 wherein said memory comprises a read only memory device.

7. The apparatus according to claim 6 wherein said memory comprises a programmable read only memory device.

8. The apparatus according to claim 1 wherein said memory comprises a memory latch circuit.

9. A beam steering system for an ultrasonic diagnostic apparatus comprising, in combination:
   a plurality of ultrasound transducers for receiving acoustical echo signals generated by ultrasonic beam reflections and for producing electrical outputs representative of said echo signals;
   means for processing said outputs to provide a diagnostic image;
   a plurality of variable delay circuits for coupling the electrical outputs from each said transducer to said processing means, each said variable delay circuit including a tapped analog delay line having an input connected to receive the output from one of said transducers and a plurality of output taps, said circuit further including an analog switch connected to each said tap and to a common output coupled to said processing means and a memory storing switch control codes representing states of said analog tap switches, said memory including an output connected to control said switches; and
   a scan control circuit connected to said memories of said variable delay circuits and constructed and arranged to generate a succession of scan signals each of which represents a particular beam direction, each of said signals operating to access an address of said memories and to apply the switch control code stored at said address to the associated analog tap switches, whereby the outputs of said transducers are phased in a predetermined time sequence to represent echo signals emanating from reflection sources oriented at a specified deflection angle relative to said transducers, said angle being controlled by said scan control circuit.

10. The apparatus according to claim 9 wherein said tapped analog delay line comprises a first delay line having an intertap delay time approximately equal to a quantum delay time and a second delay line having an intertap delay time approximately equal to the overall delay time of said first delay line and an overall delay time longer than that of said first delay line and having the delay time required to give a maximum deflection angle of the ultrasonic beam directivity.

11. The apparatus according to claim 10 wherein said first and second analog delay lines are each provided with 16 taps.

12. The apparatus according to claim 9 wherein said tapped analog delay line comprises an LC delay line.

13. The apparatus according to claim 9 wherein said memory comprises a read only memory device.

14. The apparatus according to claim 13 wherein said memory comprises a programmable read only memory device.

15. The apparatus according to claim 9 wherein said memory device comprises a memory latch circuit.

16. The apparatus according to claim 9 wherein said tapped analog delay line, said switches and said memory are arranged proximate to each other on a common circuit board.

17. A beam steering system for an ultrasonic diagnostic apparatus comprising, in combination:
   a plurality of ultrasound transducers for generating an ultrasonic beam;
   pulse generating means for energizing said transducers to emit a sequence of pulses of ultrasonic energy;
   a plurality of variable delay circuits for coupling said pulse generating means to each of said transducers, each said variable delay circuit including a tapped analog delay line having an input connected to receive the output of said pulse generating means and a plurality of output taps, said circuit further including an analog switch connected to each said tap and to a common output coupled to one of said transducers and a memory storing switch control codes representing states of said analog tap switches, said memory including an output connected to control said switches and said switch control codes being derived by measuring the delay time for each tap of the respective tapped analog delay lines against a series of delay times known to be required for producing specified beam directions; and a scan control circuit connected to said memories of said variable delay circuits and constructed and arranged to generate a succession of scan signals each of which represent a particular beam direction, each of said signals operating to access an address of said memories and to apply the switch control code stored at said address to the associated analog tap switches, whereby said transducers are pulsed at predetermined times for generating an ultrasonic beam in a direction controlled by said scan control circuit.

* * * * *